US012667847B2

(12) United States Patent
 Ohsaka

(10) Patent No.: US 12,667,847 B2
(45) Date of Patent: Jun. 30, 2026

(54) CELL SCREENING DEVICE AND CELL SCREENING KIT

(71) Applicant: Tokyo Ohka Kogyo Co., Ltd., Kawasaki (JP)

(72) Inventor: Takashi Ohsaka, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 678 days.

(21) Appl. No.: 17/639,500

(22) PCT Filed: Sep. 28, 2020

(86) PCT No.: PCT/JP2020/036545
§ 371 (c)(1),
(2) Date: Mar. 1, 2022

(87) PCT Pub. No.: WO2021/065771
PCT Pub. Date: Apr. 8, 2021

(65) Prior Publication Data
US 2022/0297127 A1 Sep. 22, 2022

(30) Foreign Application Priority Data

Sep. 30, 2019 (JP) ................................. 2019-178989

(51) Int. Cl.
*B01L 3/00* (2006.01)
*C12M 1/12* (2006.01)
(Continued)

(52) U.S. Cl.
CPC ....... *B01L 3/502761* (2013.01); *C12M 23/12* (2013.01); *C12M 23/44* (2013.01);
(Continued)

(58) Field of Classification Search
None
See application file for complete search history.

(56) References Cited

U.S. PATENT DOCUMENTS

| | | | | |
|---|---|---|---|---|
| 5,961,799 A | * | 10/1999 | Matsumoto | ........ G01N 27/3271 |
| | | | | 422/504 |
| 2002/0182645 A1 | * | 12/2002 | Miltenyi | ............ G01N 33/5005 |
| | | | | 435/325 |

(Continued)

FOREIGN PATENT DOCUMENTS

| | | |
|---|---|---|
| CN | 103415774 A | 11/2013 |
| CN | 107407691 A | 11/2017 |

(Continued)

OTHER PUBLICATIONS

International Search Report in International Application No. PCT/JP2020/036545 mailed on Nov. 17, 2020.

(Continued)

*Primary Examiner* — Neil N Turk
*Assistant Examiner* — Benjamin Joseph Kass
(74) *Attorney, Agent, or Firm* — Knobbe, Martens, Olson & Bear, LLP

(57) ABSTRACT

A cell screening device having a bottom plate part; a cell placement membrane provided on the bottom plate part and forming a cell placement surface; a pair of fluid injection parts provided on the bottom plate part and partitioned from the cell placement membrane; and a flow channel provided between the bottom plate part and the cell placement membrane and having flow channel end portions extending to the fluid injection parts. On the cell placement surface of the cell placement membrane are formed a plurality of wells having a size that enables the wells to individually accommodate cells to be screened, and through holes extending from the inner bottom surfaces of the wells and communicating with the flow channel.

5 Claims, 10 Drawing Sheets

(51) Int. Cl.
　　*C12M 1/26*　　　(2006.01)
　　*C12M 1/32*　　　(2006.01)
　　*C12M 3/00*　　　(2006.01)
(52) U.S. Cl.
　　CPC ............ *C12M 25/02* (2013.01); *C12M 33/14* (2013.01); *B01L 2200/025* (2013.01); *B01L 2200/0652* (2013.01); *B01L 2200/0689* (2013.01); *B01L 2200/16* (2013.01)

(56)　　　　References Cited

U.S. PATENT DOCUMENTS

| | | | |
|---|---|---|---|
| 2013/0345088 A1 | 12/2013 | Noji et al. | |
| 2016/0045884 A1* | 2/2016 | Husain | B01L 3/50857 506/40 |
| 2016/0289669 A1 | 10/2016 | Fan et al. | |
| 2017/0067006 A1 | 3/2017 | Obi | |
| 2017/0189907 A1* | 7/2017 | Tibbe | B01L 3/5085 |
| 2018/0282677 A1 | 10/2018 | Ohsaka et al. | |
| 2019/0366340 A1* | 12/2019 | Govyadinov | F16K 99/0019 |
| 2020/0123484 A1 | 4/2020 | Tseng | |
| 2020/0362294 A1 | 11/2020 | Suzuki et al. | |
| 2022/0113233 A1* | 4/2022 | Kato | G01N 37/00 |
| 2022/0297127 A1 | 9/2022 | Ohsaka | |
| 2022/0340859 A1 | 10/2022 | Ohsaka | |

FOREIGN PATENT DOCUMENTS

| | | | | |
|---|---|---|---|---|
| CN | 110036104 A | 7/2019 | | |
| JP | A 11-509420 | 8/1999 | | |
| JP | 2017-518752 A | 7/2017 | | |
| JP | 2018-121568 A | 8/2018 | | |
| JP | 2019-146548 A | 9/2019 | | |
| WO | WO 97/04074 A1 | 2/1997 | | |
| WO | WO 2015/087370 A1 | 6/2015 | | |
| WO | WO 2015/191684 A1 | 12/2015 | | |
| WO | WO 2015/198866 A1 | 12/2015 | | |
| WO | WO 2017/057234 A1 | 4/2017 | | |
| WO | WO 2018/105608 A1 | 6/2018 | | |
| WO | WO-2019069900 A1 * | 4/2019 | .......... | B01L 3/50273 |
| WO | WO-2019167951 A1 * | 9/2019 | ............. | C12M 1/34 |
| WO | WO 2021/065765 A1 | 4/2021 | | |
| WO | WO 2021/065771 A1 | 4/2021 | | |

OTHER PUBLICATIONS

Office Action received in U.S. Appl. No. 17/753,497, dated Dec. 10, 2024.

International Search Report in International Application No. PCT/JP2020/036530 mailed on Nov. 24, 2020.

\* cited by examiner

FIG. 5

CELL SCREENING DEVICE AND CELL SCREENING KIT

TECHNICAL FIELD

The present invention relates to a cell screening device and a cell screening kit for screening cells. Priority is claimed on Japanese Patent Application No. 2019-178989, filed Sep. 30, 2019, the content of which is incorporated herein by reference.

BACKGROUND ART

In recent years, particularly in the field of drug discovery, the target of cell analysis has been subdivided from the cell group level to the single cell level, and a method has been used in which a cell screening device is used to catch cells one by one in minute wells, and then a large number of cells are subjected to a screening test at once to select cells having the desired characteristics. As the method of screening cells, for example, a method has been adopted in which cells caught in a large number of wells are brought into contact with a solution obtained by dispersing a reagent such as a capture that binds to a specific antibody, cells that have secreted a secretion product bound to the catcher are identified, and then the identified cells are recovered from the wells has been adopted.

Patent Document 1 discloses a cell screening device that was previously proposed by the present applicants and the like. This cell screening device has a first substrate and a second substrate that are disposed so as to be horizontally stacked, a large number of wells in which cells can be accommodated one by one are formed on the surface of the first substrate, and communication holes that reach the back surface of the first substrate from the bottom surfaces of the respective wells are formed individually. These communication holes are so small that cells cannot pass therethrough. On the second substrate, an accumulation part that receives the secretion product flowing out of the well through the communication hole is formed, and the secretion product and the reagent are reacted at the accumulation part to identify the target cell.

CITATION LIST

Patent Document

Patent Document 1
  PCT International Publication No. WO2017/057234A1 Pamphlet

SUMMARY OF INVENTION

Technical Problem

In a cell screening device as disclosed in Patent Document 1, it is necessary to provide a reagent introduction part in order to supply a reagent to the accumulation part. For example, in a case where a reagent introduction part that communicates with an accumulation part is provided at the end part of the device, there is the risk that a dispersion liquid or a reagent flows in the longitudinal direction of the accumulation part (called a sloshing phenomenon), a part of the dispersion liquid or reagent flows into the well through the through-hole, the cells caught in the well are lifted, and the cells are eliminated from the well, in a case where the cells are caught in the well or the cell screening device is carried or inclined from a horizontal state in a state where the accumulation part is filled with the dispersion liquid or the reagent.

Solution to Problem

A cell screening device according to an aspect [1] of the present invention includes a bottom plate part; a cell placement part that is provided on the bottom plate part and is configured to constitute a cell placement surface; a fluid injection part that is provided on the bottom plate part, separately from the cell placement part; a plurality of wells that are formed on the cell placement surface of the cell placement part and have a size in which cells to be screened are individually accommodatable; a flow channel that is provided between the bottom plate part and the cell placement part, with a flow channel end part extending to the fluid injection part; a through-hole that leads to the flow channel from an inner bottom surface of the well and has an inner diameter through which the cells to be screened are not passable; a lid part that is provided in the fluid injection part and blocks the flow channel end part; and a fluid injection port that is provided in the lid part and has an opening portion communicating with the flow channel.

According to such a cell screening device, in a case where the flow channel end part of the flow channel is blocked with a lid part, and a fluid injection port having an opening portion communicating with the flow channel is provided in this lid part, the movement of the fluid in the flow channel can be suppressed by the lid part, and the fluid can be injected in and taken out of the flow channel through the fluid injection port. As a result, even in a case where the cell screening device is carried or inclined with the cells being caught in the well of the cell screening device and a fluid such as a dispersion liquid being put into the flow channel, it becomes difficult for the fluid to excessively move along the flow channel, and it is possible to suppress the sloshing phenomenon. Accordingly, it is possible to suppress a problem in which some of the dispersion liquid flows into the well through the through-hole and the cells caught in the well are released.

In the cell screening device of an aspect [2], according to the aspect [1], a fluid storage part configured to store a fluid that overflows from the opening portion of the fluid injection port is formed in the lid part around the fluid injection port, and a partitioned part is provided between the cell placement surface and the lid part, the partitioned part preventing the fluid from flowing to the cell placement part in a case where the fluid is accumulated in the fluid storage part. In this case, even in a case where the fluid overflows from the opening portion of the fluid injection port, the fluid storage part receives the fluid, and thus it is possible to suppress the reentry into the flow channel from the fluid injection port, and it is possible to reduce the risk, for example, contamination. In addition, since the partitioned part is formed between the cell placement surface and the lid part, it is possible to suppress the flow of the fluid to the cell placement part even in a case where the fluid is accumulated in the fluid storage part.

In the cell screening device of an aspect [3], according to the aspect [1] or [2], the bottom plate part has a rectangular shape having a long side and a short side, the fluid injection part, the lid part, and the fluid injection port are each formed on both sides of the bottom plate part in a longitudinal direction, and the cell placement part is disposed between the two lid parts. In this case, a wide range of usage methods, for example, causing the fluid to flow from one of the two fluid injection ports into the flow channel and causing the excess fluid to be discharged from the other fluid injection port is possible. However, the present invention is not limited to the constitution in which two fluid injection ports are provided, and as necessary, only one fluid injection port may be provided, or three or more fluid injection ports can also be provided.

In the cell screening device of an aspect [4], according to any one of the aspects [1] to [3], the cell placement part is a membrane body, a plurality of the wells are formed on an upper surface of the membrane body in a lattice form, and the through-hole that leads to the inner bottom surface of each of the wells is formed on a lower surface of the membrane body, a frame body that supports a periphery of the membrane body and surrounds the cell placement surface is provided, and an engaging part for attachably and detachably fixing the frame body is provided in the bottom plate part. In this case, in a case where a frame body is engaged with an engaging part of the bottom plate part, the membrane body having the wells is positioned at the correct position on the bottom plate part, and the frame body can be removed from the bottom plate part after screening.

In the cell screening device of an aspect [5], according to any one of the aspects [1] to [4], a peripheral wall portion that stands up from a circumference of the lid part is formed, and the lid part and the peripheral wall portion are formed as an outer frame body that is attachable to and detachable from the bottom plate part. In this case, the lid part and the peripheral wall portion can be accurately positioned simply by forming the bottom plate part and the outer frame body as separate ones and attaching the outer frame body to the bottom plate part, and thus assembly is easy. In addition, after use, it is also possible to remove the outer frame body from the bottom plate part, which facilitates maintenance.

In the cell screening device of an aspect [6], according to the aspect [4], a standing peripheral wall portion is formed in a circumference of the lid part, the lid part and the peripheral wall portion are formed as an outer frame body that is attachable to and detachable from the bottom plate part, and the frame body that supports the membrane body is attachably and detachably fixed to the outer frame body. In this case, the membrane body, the lid part, and the peripheral wall portion can be accurately positioned simply by forming each of the bottom plate part, the outer frame body, and the frame body as separate ones and attaching the frame body and the outer frame body to the bottom plate part, and thus the ease of assembly can be improved. In addition, after use, it is also possible to remove the frame body and the outer frame body from the bottom plate part, which facilitates maintenance.

In the cell screening device of an aspect [7], according to any one of the aspects [1] to [5], the bottom plate part has a rectangular shape having a long side and a short side, the fluid injection part, the lid part, and the fluid injection port are each formed on both sides of the bottom plate part in a longitudinal direction, the cell placement part is disposed between the two lid parts, and the lid part, a peripheral wall portion that stands up from a circumference of the lid part, and a peripheral wall portion that surrounds a periphery of the cell placement part are formed as an outer frame body that is attachable to and detachable from the bottom plate part. In this case, the cell placement part, the lid part, peripheral wall portion, and two fluid injection ports can be accurately positioned simply by forming each of the bottom plate part and the outer frame body as separate ones and attaching the outer frame body to the bottom plate part, and thus the ease of assembly can be improved. In addition, after use, disassembly can be easily carried out by removing the outer frame body from the bottom plate part, which facilitates maintenance.

In the cell screening device of an aspect [8], according to any one of the aspects [1] to [7], the fluid injection port has a cylindrical shape that stands up from an upper surface of the lid part. In this case, since the fluid injection port has a cylindrical shape, it is easy to tale in and take out the fluid by almost airtightly applying a conical pointed tip of a pipette or a dispenser.

In the cell screening device of an aspect [9], according to any one of the aspects [1] to [8], in the lid part, a bubble discharge surface is formed on at least a part of a ceiling surface of the flow channel end part, the bubble discharge surface rising in an inclined surface shape or a stepped shape as the bubble discharge surface approaches the fluid injection port. In this case, since an inclined surface rising toward the fluid injection port or an air bubble discharge surface having a stepped shape is formed on the ceiling surface on the back side of the lid part, the air bubbles that have entered the flow channel are easily discharged from the fluid injection port, and thus problems due to air bubbles can be suppressed.

The cell screening kit of an aspect [10 includes the cell screening device according to any one of the aspects of [1] to [9], and a detection particle that is a carrier particle on which a substance having a binding property to a secretion product of cells to be screened is immobilized. According to this cell screening kit, in a state where cells are incorporated into individual wells, detection particles and a secretion product of cells are reacted in the wells, and screening can be carried out by luminescence from the detection particles. Moreover, as a result, even in a case where the cell screening device is carried or inclined with a fluid such as a dispersion liquid being put into the flow channel, it becomes difficult for the fluid to move along the flow channel, and it is possible to suppress the sloshing phenomenon. Accordingly, it is possible to suppress a problem in which some of the dispersion liquid flows into the well through the through-hole and the cells or the detection particles caught in the well are released from the well.

Advantageous Effects of Invention

As described above, according to the cell screening device or the cell screening kit of the present invention, even in a case where the cell screening device is carried or inclined with the cells being caught in the well of the cell screening device and a fluid such as a dispersion liquid being put into the flow channel, it becomes difficult for the fluid to move along the flow channel, whereby the sloshing phenomenon is suppressed, and an excellent effect of suppressing a problem, for example, in which some of the dispersion liquid flows into the well through the through-hole and the cells or the detection particles caught in the well are released, is exhibited.

BRIEF DESCRIPTION OF DRAWINGS

FIG. 5 is a real cross-sectional view of an end part of the cell screening device according to the same embodiment.

DESCRIPTION OF EMBODIMENTS

Figure 5:
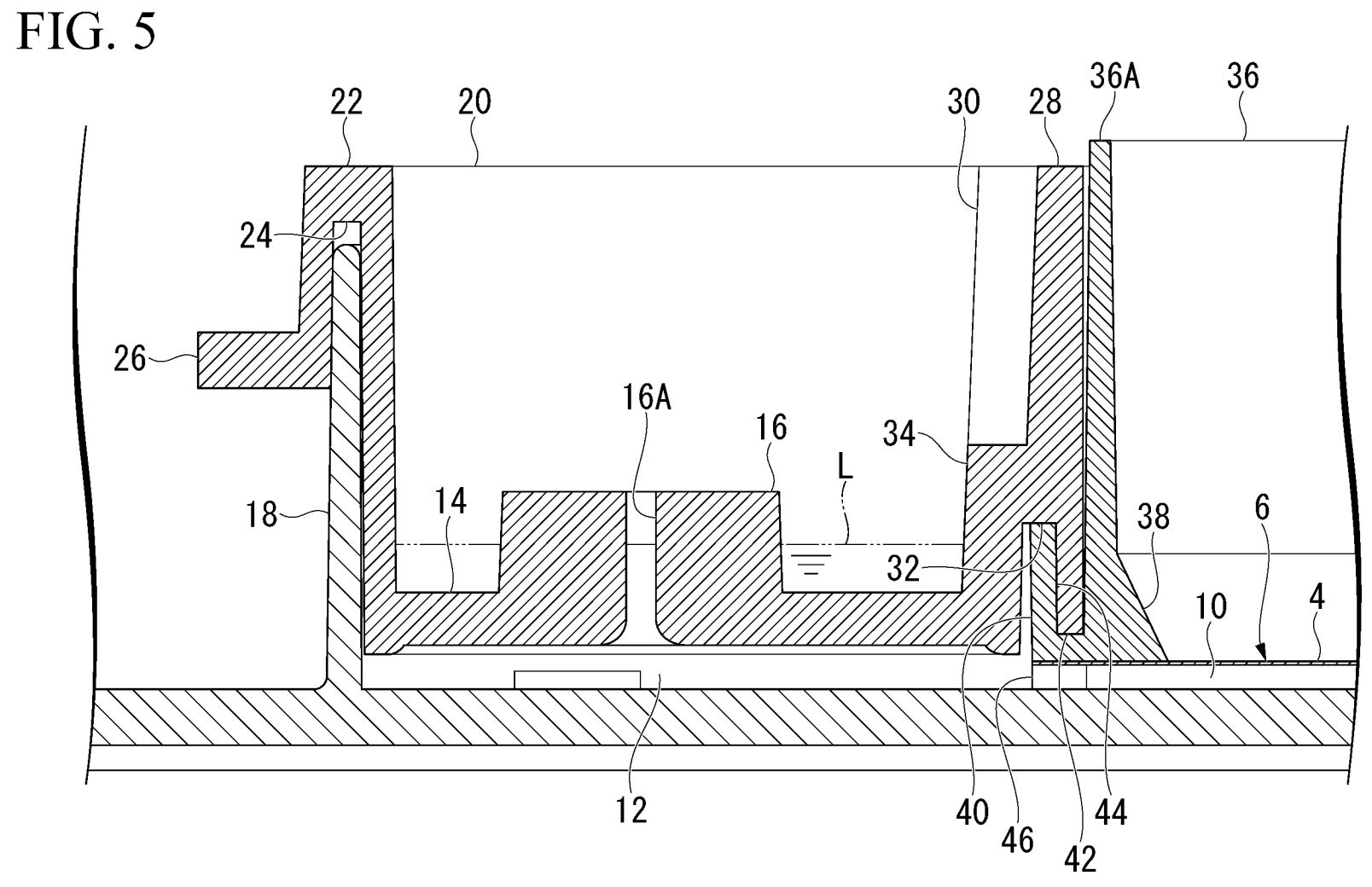
Figure 6:
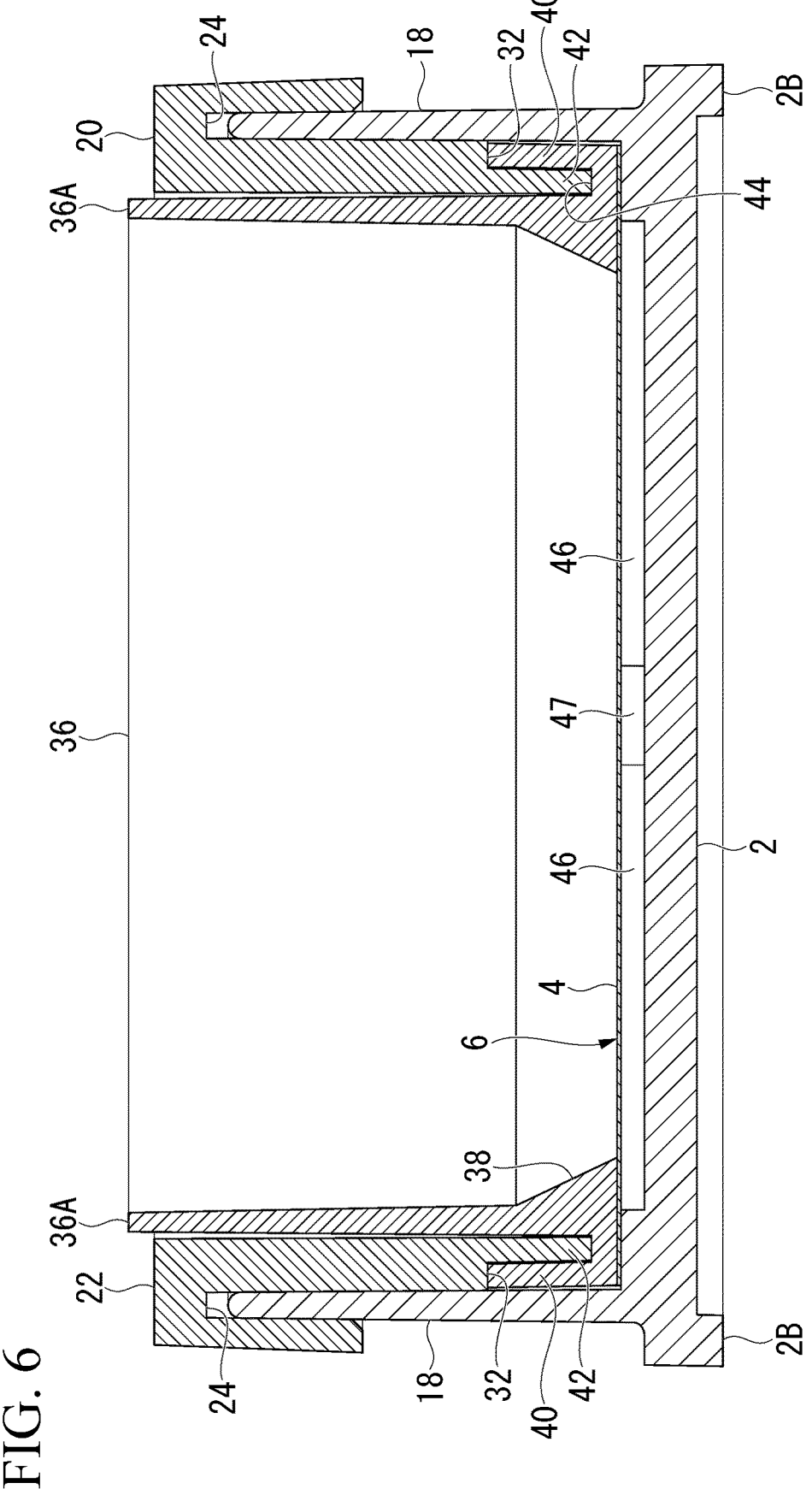
FIG. 6 is a side sectional view of the cell screening device according to the same embodiment.
Figure 7:
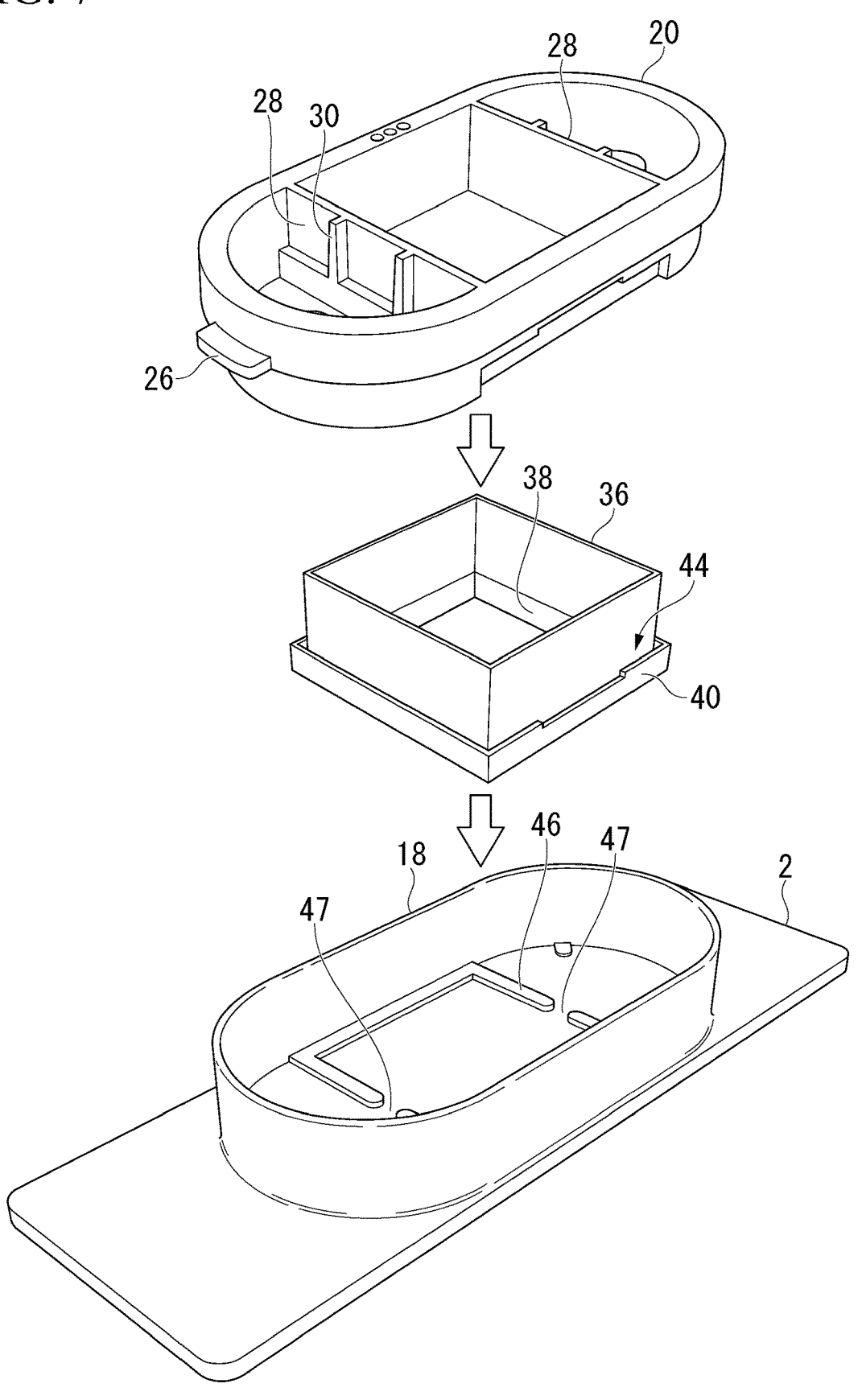
FIG. 7 is a perspective view showing an assembly method of the cell screening device according to the same embodiment.
Figure 8:
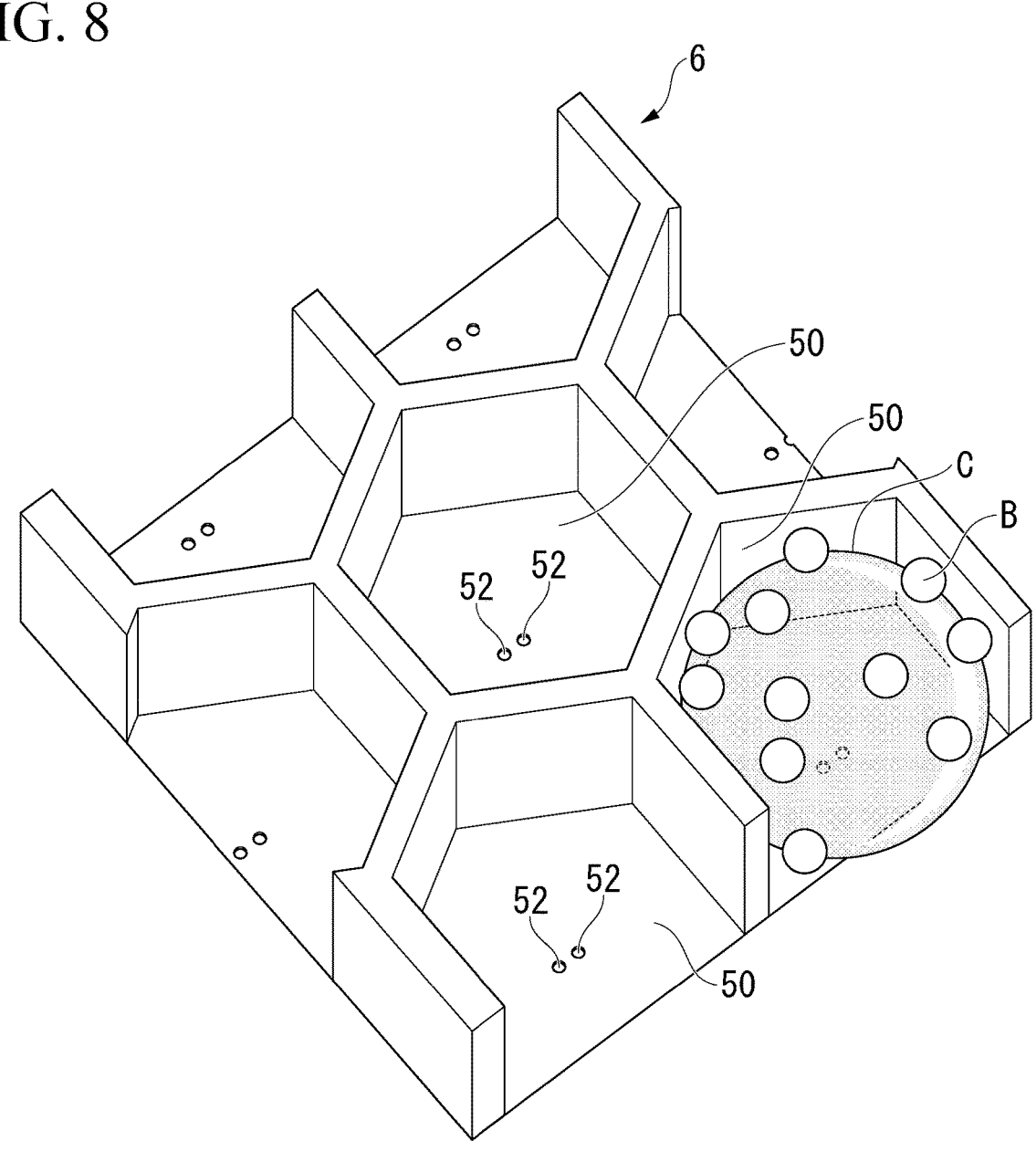
FIG. 8 is an enlarged perspective view showing a cell placement membrane (a cell placement part) and a well of the cell screening device according to the same embodiment.

FIG. 1 to FIG. 6 all show a completed state of a cell screening device 1 according to the embodiment of the present invention, and FIG. 7 shows a method of assembling the cell screening device 1. A cell screening device 1 of this embodiment has a bottom plate part 2; a cell placement membrane (a cell placement part) 6 that is provided on the bottom plate part 2 and is configured to constitute a cell placement surface 4; a pair of fluid injection parts 8 that are provided on the bottom plate part 2, separately from the cell placement membrane 6; and a flow channel 10 that is provided between the bottom plate part 2 and the cell placement membrane 6, a flow channel end part 12 of which extends to the fluid injection part 8. On the cell placement surface 4 of the cell placement membrane 6, for example, as shown in FIG. 8, a plurality of wells 50 having a size capable of individually accommodating cells C to be screened, and a through-hole 52 that leads to the flow channel 10 from the inner bottom surface of the wells 50 are formed. The through-hole 52 has an inner diameter through which the cells C to be screened cannot pass.

Hereinafter, the structure of the cell screening device 1 will be described in detail. The bottom plate part 2 of this example has an elongated rectangular plate shape having a constant thickness, and the four corners are chamfered. A small ridge 2B is formed on the bottom plate part 2 over the entire circumference along the outer circumference of the bottom surface. The shape of the bottom plate part 2 is not limited to the one shown in the drawing, and it may be any shape such as a disk shape, an elliptical shape, or a square shape. In a case where a horizontal flow channel 10 can be formed, the thickness of the bottom plate part 2 may not be constant. Generally, it is desirable that, in terms of molding accuracy and cost, the bottom plate part 2 be made of various plastics that are harmless to the target cells; however, as necessary, it may be made of any material such as ceramic, glass, or metal. The surface of the bottom plate part 2 may be subjected to some kind of coating for alleviating the influence on cells.

Figure 3:
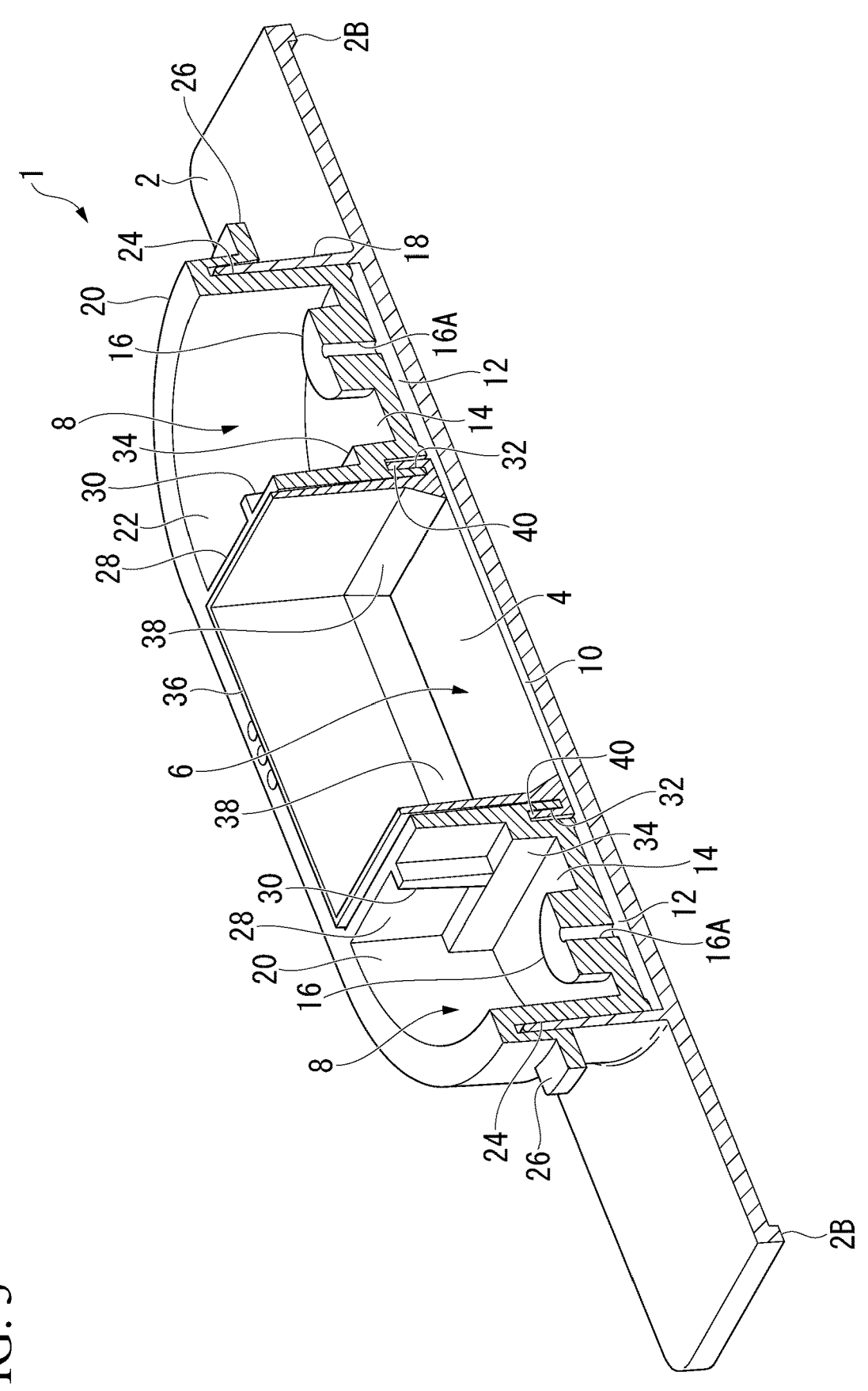
FIG. 3 is a perspective view showing a real cross section of the cell screening device according to the same embodiment.

As shown in FIG. 3, on the upper surface of the bottom plate part 2, an engagement wall 18 having a rectangular shape, both ends of which have a semicircular shape in plan view, is integrally formed to surround the central part in a state of vertically standing up from the bottom plate part 2. The shape of the engagement wall 18 is not limited to the shape shown in the drawing, and it may be a simple rectangular shape, a circular shape, an elliptical shape, or the like. The height of the engagement wall 18 in this example is set to be equal over the entire circumference. A second frame body 20 is attachably and detachably attached to the engagement wall 18 to cover the engagement wall 18 from above over the entire circumference.

The second frame body 20 has a rectangular peripheral wall portion 22 having a rectangular shape, both ends of which have a semicircular shape in plan view, and a pair of partitioned parts 28 provided parallel to each other on the inner circumference side of the peripheral wall portion 22, and the whole is integrally formed. The material of the second frame body 20 is not limited, and it is generally desirable that, in terms of molding accuracy and cost, the second frame body 20 be made of various plastics that are harmless to the target cells; however, as necessary, it may be made of any material such as ceramic, glass, or metal. A rectangular parallelepiped space is opened between the partitioned part 28 and the partitioned part 28, and the cell placement membrane 6 is disposed in this space.

The upper end of the peripheral wall portion 22 of the second frame body 20 has a cross-sectional shape in which it is folded outward over the entire circumference, and inside this folded portion, a narrow engagement groove 24 that opens downward is formed at a constant depth over the entire circumference. The upper end part of the engagement wall 18 is inserted into the engagement groove 24 over the entire circumference, and elastically tightened at the folded portion of the peripheral wall portion 22, whereby the second frame body 20 is attachably and detachably fixed to the engagement wall 18. Protrusions 26 that protrude horizontally are formed at both tips of the second frame body 20 in the longitudinal direction, and in a case where these protrusions 26 are lifted with a fingertip, the engagement wall 18 comes out from the engagement groove 24, whereby the bottom plate part 2 can be separated from the second frame body 20.

Each semicircular region surrounded by the peripheral wall portion 22 of the second frame body 20 and each partitioned part 28 serves as the fluid injection part 8. In these fluid injection parts 8, the lid part 14 having a semicircular shape is formed in parallel with the bottom plate part 2 so that the lower end of the peripheral wall portion 22 and the lower end of each partitioned part 28 are connected. A flow channel end part 12 that is both ends of the flow channel 10 is formed between the lid part 14 and the bottom plate part 2, and the lid part 14 has a structure that airtightly blocks the flow channel end part 12. Since the lid part 14 is formed in this manner, the flow channel end part 12 that is both ends of the flow channel 10 is sealed, which prevents a fluid excessively flowing sideways through the flow channel 10 and the flow channel end part 12 even in a case where the cell screening device 1 is inclined or shaken. In this example, the thickness of the flow channel end part 12 in the vertical direction is constant; however, it may be partially changed as necessary, as in the embodiment of FIG. 10 described later.

In this embodiment, an opening portion 16A having a circular shape is formed in one place at a substantially center of each lid part 14, and a fluid injection port 16 having a circular shape is formed upright from each lid part 14 in a manner matching with the opening portion 16A. The surface of the lid part 14 around the fluid injection port 16 serves as a fluid storage part, and as shown in FIG. 5, a fluid L overflowing from the fluid injection port 16 is accumulated. As the fluid storage part, a recessed part may be proactively formed around the fluid injection port 16 on the upper surface of the lid part 14.

In this embodiment, the fluid injection port 16 is caused to stand up from the lid part 14. However, instead, the fluid injection port formed in the lid part 14 is made to be an opening portion that does not protrude upward and a recessed part that surrounds this opening portion, which has an annular shape or the like, is formed on the surface of the lid part 14, and then this recessed part can be used as the fluid storage part.

The opening portion 16A of the fluid injection port 16 is formed in a caliber that matches well with a tip of an instrument such as a pipette, a micropipette, or a dispenser for injecting a fluid (a reagent or a dispersion liquid) from the fluid injection port 16, and thus the pointed tip of the instrument can airtightly abut with the opening portion 16A of the fluid injection port 16. The shape of the fluid injection port 16 is not limited to a cylindrical shape. It may be a rectangular tubular shape or a polygonal tubular shape as necessary, and may be an annular shape in which the periphery of the opening portion 16A is slightly raised, or simply the opening portion as described above. In addition, the fluid injection port 16 may be an inverted conical opening portion formed by denting the surface of the lid part 14.

At a lower end of a partitioned part 28 on the side of the fluid injection part 8, a step portion 34 having a constant height from the lower surface is formed over the entire length of the partitioned part 28, and above the step portion 34, each of two ribs 30 that reach the upper end of the partitioned part 28 is formed to extend in the vertical direction. The rib 30 enhances the bending strength of the partitioned part 28. In addition, in the partitioned part 28, each of an engagement groove 32 having a constant depth, opening on the lower surface of the step portion 34, and an engagement ridge 42 adjacent to the engagement groove 32 on the side of the cell placement membrane 6 is formed.

As shown in FIG. 6, the engagement groove 32 having a constant depth, opening on the lower surface of the peripheral wall portion 22, and the engagement ridge 42 adjacent to the engagement groove 32 on the side of the cell placement membrane 6 are also formed at two linearly extending places in the peripheral wall portion 22 of the second frame body 20. The engagement groove 32 and engagement ridge 42 at the two linearly extending places are respectively connected to the engagement groove 32 and the engagement ridge 42 of the partitioned part 28, thereby forming a rectangular shape when viewed in plan view.

A rectangular tubular first frame body 36 having a rectangular shape in plan view is attachably and detachably accommodated in a square space surrounded by two linearly extending places in the peripheral wall portion 22 and two partitioned parts 28. As shown in FIG. 8, the cell placement membrane 6 is stretched over the entire surface of the lower end of the first frame body 36 with the wells 50 facing upward, and the lower end of the first frame body 36 and the cell placement membrane 6 are all joined without any gaps over the entire circumference. The first frame body 36 is made of a flexible plastic or the like, and thus it is configured such that in a case where a force to spread the first frame body 36 outward is applied, four walls thereof slightly spread outward, tension is applied to the cell placement membrane 6, and slack in the cell placement membrane 6 can be prevented.

The thickness of the cell placement membrane 6 is not limited. However, it is preferably set to be about 5 to 100 μm and more preferably about 10 to 50 μm from the viewpoints of forming a well 50 which target cells enter one by one and forming a fine through-hole 52 that allows a fluid to flow from the bottom of the well 50 to the back surface side. The cell placement membrane 6 may be a multilayer membrane having two or more layers. In that case, a through-hole to be the well 50 is formed in the upper layer, a through-hole to be the through-hole 52 is formed in the lower layer, and then these two layers are bonded together to form the well 50 and the through-hole 52.

The material of the cell placement membrane 6 is not limited, and it is generally desirable that, in terms of molding accuracy and cost, the cell placement membrane 6 be made of various plastics that are harmless to the target cells; however, as necessary, it may be made of any material such as an inorganic compound such as ceramic, polycrystal or single crystal silicon, or glass, or a metal. The well 50 and the through-hole 52 can also be formed by etching or photolithography.

From the viewpoint of increasing the disposition density according to the average shape of the cells C to be captured, the planar shape of the well 50 is preferably hexagonal or circular as shown in FIG. 8; however, as necessary, it may be quadrangular such as square, or polygonal, elliptical, or the like. The size of the well 50 should be selected according to the size of the cells C to be caught, and thus it is not limited. However, in general, it is desirable that the maximum diameter of the circle that enters the well opening portion be about 1 to 100 μm and the depth thereof be about 1 to 100 μm so that one cell C enters one well 50, but two or more cells C hardly enter one well 50. A plurality of kinds of first frame bodies 36 having the cell placement membranes 6, differing in the size of the well 50, may be prepared and combined with a common bottom plate part 2 and the second frame body 20 to constitute a cell screening kit.

Regarding the size of the cells C, the maximum diameter of the circle that enters the well 50 in plan view may be about 0.5 to 2 times and is more preferably 0.8 to 1.9 times the maximum diameter of the cells C to be collected. The depth of the well 50 may be about 0.5 to 4 times and more preferably 0.8 to 1.9 times the maximum diameter of the cells C to be collected. It is preferable that the shortest distance between the well 50 and the wells 50 adjacent to each other be about 1 to 10 μm since the density of the wells 50 can be increased; however, this range is not limited to this.

Two through-holes 52 in this example are formed in the center of the bottom surface of each well 50. It is preferable that a plurality of through-holes be formed in this manner since clogging is unlikely to occur. However, the present invention is not limited to this, and in the present invention, one through-hole or three or more through-holes may be formed in the center of one well 50, or a plurality of through-holes 52 may be formed at random or at lattice point positions on the bottom surface of the well 50. The inner diameter of the through-hole 52 is not limited. However, the minimum inner diameter is preferably in a range of about 10 nm to 20 μm so that the cells C do not pass through, and it is preferably 0.5 times or less the average diameter of the cells C to be caught in the well 50.

Figure 4:
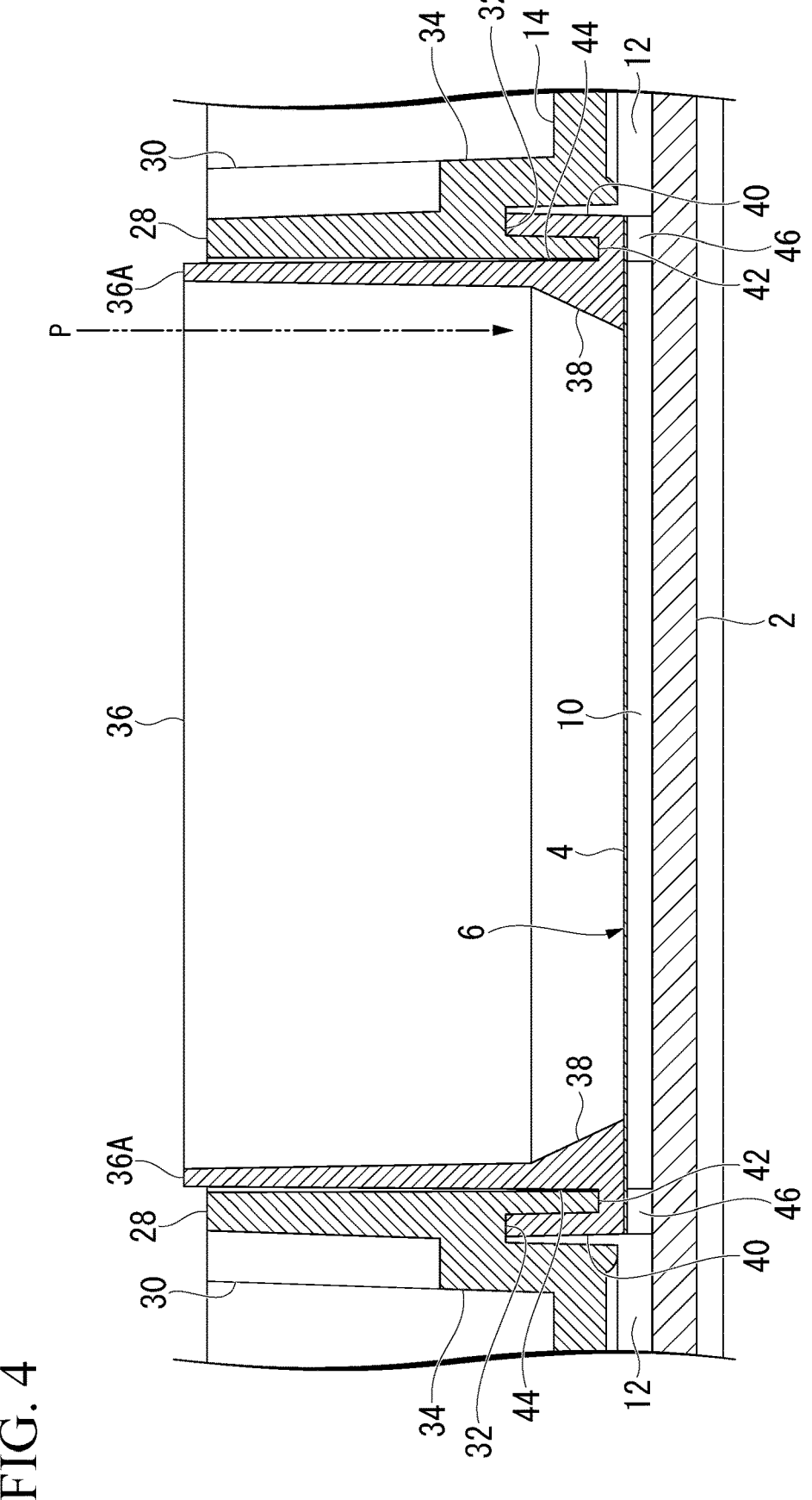
FIG. 4 is a real cross-sectional view of a central part of the cell screening device according to the same embodiment.

As shown in FIG. 4 and FIG. 6, on the outer circumference surface of the lower end part of the first frame body 36, an engagement groove 44 that opens upward and an engagement ridge 40 that protrudes downward are formed over the entire circumference by making the shape thereof folded upward. The depth of the engagement groove 44 and the vertical width of the engagement ridge 40 are substantially constant over the entire circumference of the first frame body 36. The engagement ridge 40 is inserted into the engagement groove 32 formed on the lower surface of the second frame body 20, and the engagement ridge 42 of the second frame body 20 is inserted into the engagement groove 44 of the first frame body 36. By these fittings, the first frame body 36 is fixed to the second frame body 20 in a state where the first frame body 36 is accommodated inside the central space of the second frame body 20.

At this time, the lower end surface of the first frame body 36 is abutted on the upper surface of the spacer 46 formed in the bottom plate part 2, and the thickness of the spacer 46 causes the separation amount of the cell placement membrane 6 from the bottom plate part 2, that is, the thickness of the flow channel 10 to be accurately defined. In this embodiment, as shown in FIG. 7, a pair of spacers 46 having a U-shape in plan view are formed inside the engagement wall 18 along the lower end shape of the first frame body 36, and a notch 47 is formed between the spacers 46. In a state where the first frame body 36 is fixed on the bottom plate part 2, it is configured such that a fluid flows from the flow channel 10 to each flow channel end part 12 through these notches 47. The spacer 46 may not have the shape as shown in the drawing, and it suffices that the spacer abuts with the lower surface of the first frame body 36 at several places. In some cases, it may be configured so that the height of the first frame body 36 from the bottom plate part 2 is accurately defined by the engagement with the second frame body 20 without forming the spacer 46.

An inclined surface 38 having a constant width is formed on the inner circumference surface of the lower end part of the first frame body 36 over the entire circumference, and the inclined surface 38 protrudes toward the cell placement membrane 6 as it goes downward. Due to the formation of such an inclined surface 38, in a case where target cells are sucked up from the well 50 of the cell placement membrane 6 with an instrument P such as a pipette, a micropipette, or a dispenser, it is possible to easily suck out the cells with the instrument P even in a case where the well 50 in which the collected cells are present is located just near the inner circumference of the first frame body 36 as shown in FIG. 4. Further, the inclined surface 38 also has an effect of increasing the adhesion area of the cell placement membrane 6 to the first frame body 36 and thus increasing the joining strength of the cell placement membrane 6, and it is also useful for increasing the strength of the first frame body 36.

Figure 1:
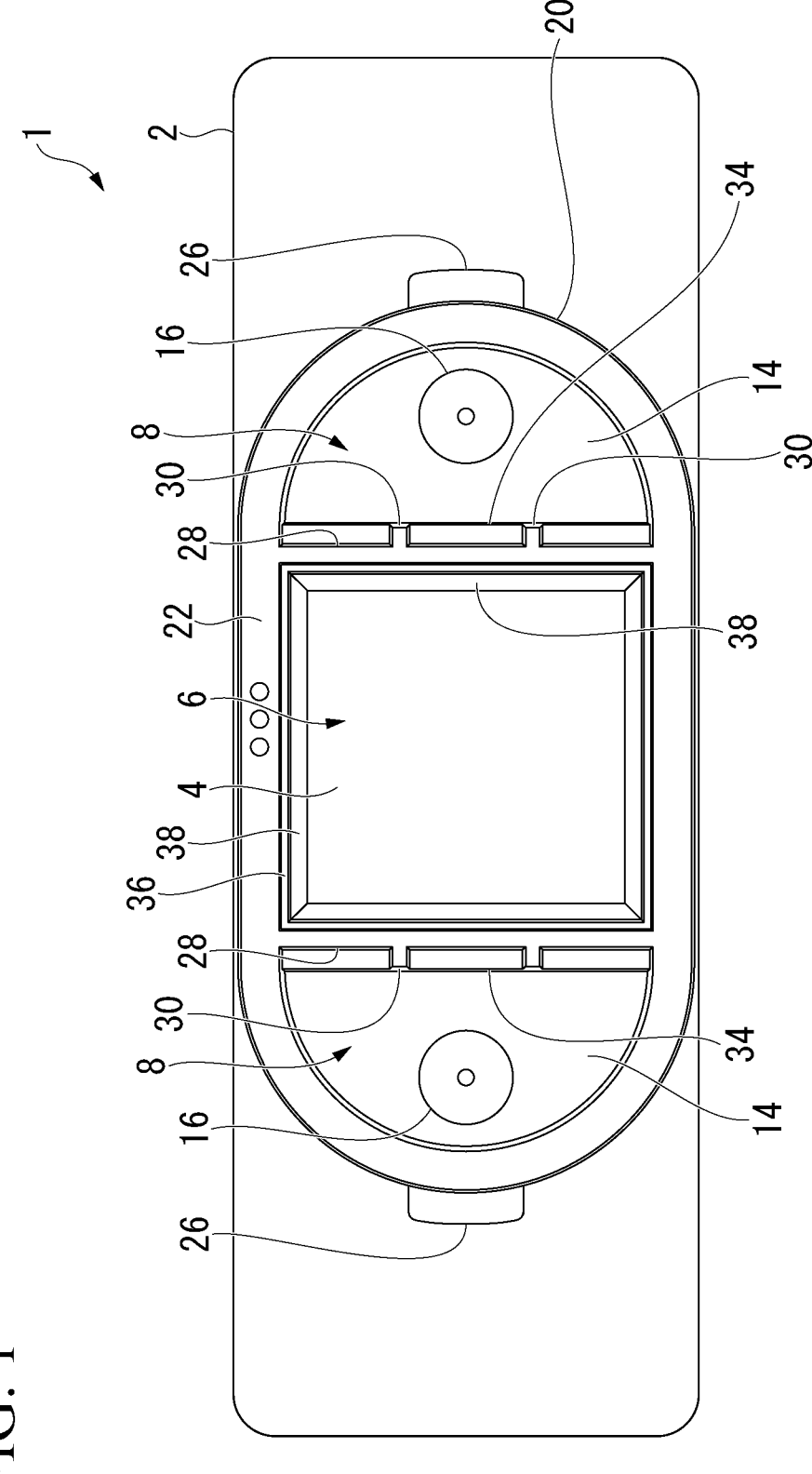
FIG. 1 is a plan view showing a cell screening device according to an embodiment of the present invention.
Figure 2:
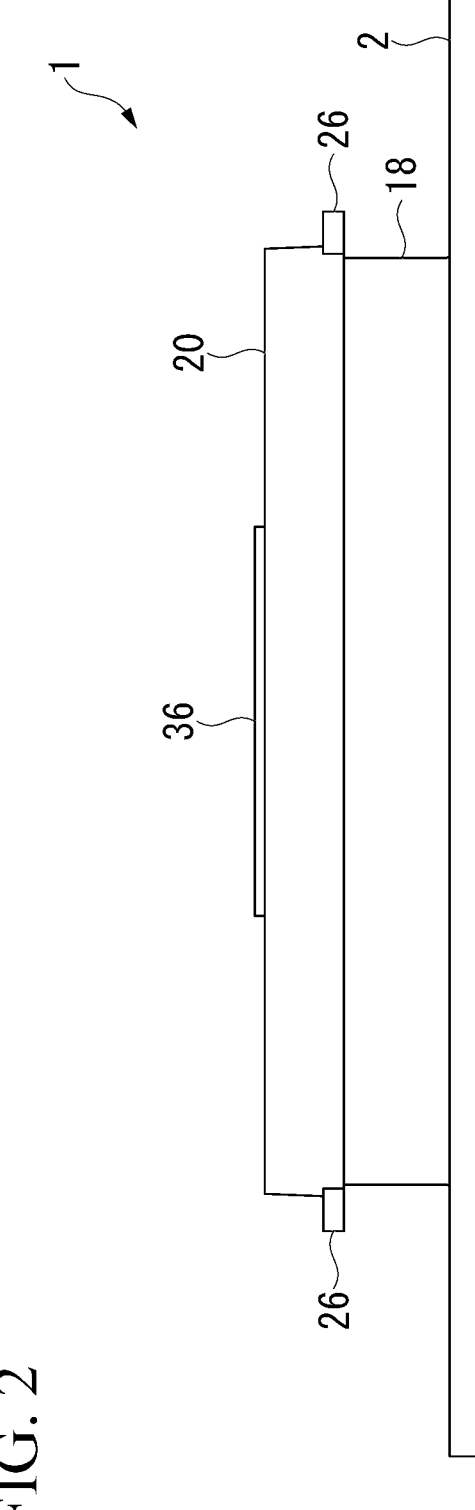
FIG. 2 is a front view of the cell screening device according to the same embodiment.

In a case of manufacturing a cell screening device having the above constitution, in a state where the bottom plate part 2, the first frame body 36, and the second frame body 20 have been individually formed as shown in FIG. 7, first, the first frame body 36 is fitted into the lower surface of the second frame body 20, and then second frame body 20 is fitted into the engagement wall 18 of the bottom plate part 2, whereby the completed state as shown in FIG. 1 and FIG. 6 is obtained.

In the process of fitting the first frame body 36 into the lower surface of the second frame body 20, as shown in FIG. 4 and FIG. 6, the engagement ridge 42 of the second frame body 20 is fitted into the engagement groove 44 of the first frame body 36, and the engagement ridge 40 of the first frame body 36 is fitted into the engagement groove 32 of the second frame body 20, whereby both are firmly fixed by the elasticity of each engaging part. At the same time, the inner circumference surface of the engagement ridge 40 and the outer circumference surface of the engagement ridge 42 have a shape in which at least one of them is slightly inclined upward as it goes upward. As a result, as the engagement progresses, the engagement ridges 40 on the four sides of the first frame body 36 are pulled outward by the engagement ridges 42 of the second frame body 20, the lower end part of the first frame body 36 is slightly expanded in all directions, and this causes tension to pull the four sides of the cell placement membrane 6, whereby a uniform tension is applied to the cell placement membrane 6.

As a result, even in a case where there is slight slack in the cell placement membrane 6 when the first frame body 36 is in the free state, slack in the cell placement membrane 6 is eliminated in a case where the first frame body 36 is fixed to the second frame body 20, and the flatness of the cell placement surface 4 on which a large number of wells 50 of the cell placement membrane 6 are formed is increased, and in a case where the cell placement surface 4 is filled with a dispersion liquid in which cells are dispersed, and then the cells are made to float evenly, for example, by shaking the cell screening device, it is possible to obtain an advantage in that it is easy to capture the cells one by one in the wells 50.

A cell screening kit using the present embodiment includes a cell screening device 1 and a bead (a detection particle) B that is a carrier particle on which a substance having a binding property to a secretion product of cells to be screened is immobilized. The cell screening kit is a product that accommodates, in an outer container such as a box, one or more cell screening devices 1 and an inner container in which a large number of fine beads B, which are detection particles, are contained in a state of powder or suspended in a dispersion liquid and encapsulated.

The kind of binding particle is not limited; however, it may be, for example, a carrier particle consisting of a bead (a magnetic bead, a resin bead, or the like), a hydrogel particle (sodium alginate gel, agarose gel, or the like), a metal particle (a gold nanoparticle), and the like, or a catcher capable of binding to an antibody that is secreted from an antibody-producing target cell, where the antibody is attached to a carrier particle. The particle size of the binding particle is not limited; however, in general, the maximum diameter of the particle is preferably 100 nm to 50 μm and more preferably about 500 nm to 30 μm.

In a case of carrying out actual screening, cells and the beads B, which are the detection particles, are dispersed in a dispersion liquid and applied onto the cell placement membrane 6, the cell screening device 1 is shaken or the cells C are discharged to the flow channel 10 through the through-hole 52 to put the cells C one by one into the well 50, and a large number of beads B are put into the well 50 together with each cell C, and the excess dispersion liquid is discharged to the flow channel 10 through the through-hole 52. In a case where the antibody in the secretion product of the cell C is reacted with the catcher of the beads B in this state, only the reacted beads B can be visualized with a fluorescently labeled antibody to find the target cell.

According to the cell screening device 1 having the above constitution, since the flow channel end parts 12 located at both ends of the flow channel 10 are blocked by lid parts 14, and the fluid injection port 16 having the opening portion 16A communicating with the flow channel 10 is provided in these lid parts 14, the movement of the fluid in the flow channel end part 12 and the flow channel 10 can be suppressed by the lid part 14, and the fluid can be injected in and taken out of the flow channel 10 through the fluid injection port 16. As a result, even in a case where the cell screening device 1 is carried or inclined with the cells C being caught in the well 50 of the cell screening device 1 and a fluid such as a dispersion liquid being put into the flow channel 10, it becomes difficult for the fluid to move along the flow channel 10 and the flow channel end part 12, and it is possible to suppress the sloshing phenomenon. Accordingly, it is possible to suppress the problem in which some of the dispersion liquid flows into the well 50 through the through-hole 52 and the cells C and the beads B caught in the well 50 are released.

Further, in this embodiment, even in a case where the fluid L overflows from the opening portion 16A of the fluid injection port 16, the fluid storage part (the upper surface of the lid part 14) receives the fluid, whereby it is possible to suppress the reentry into the flow channel 10 from the fluid injection port 16, and it is possible to reduce, for example, the risk of contamination from the outside. In addition, since the partitioned part 28 is formed between the cell placement surface 4 and the lid part 14, it is possible to suppress the flow of the fluid to the cell placement part 6 even in a case where the fluid is accumulated in the fluid storage part 14.

Further, in this embodiment, since the two fluid injection ports 16 are formed at both ends of the flow channel 10, it is possible to realize a wide range of usage methods, for example, causing the fluid to flow from one fluid injection port 16 into the flow channel 10 and causing the excess fluid to be discharged from the other fluid injection port 16.

Further, in this embodiment, since the cell placement membrane 6 is positioned at the correct position on the bottom plate part 2 by causing the lower end of the first frame body 36 to abut with the spacer 46 of the bottom plate part 2, the flow of the fluid between the well 50 and the flow channel 10 becomes as desired, and highly accurate screening becomes possible.

Further, in this embodiment, since the bottom plate part 2 and the second frame body 20 are formed as separate ones, and the lid part 14 and the peripheral wall portion 22 can be disposed at an accurate position with respect to the bottom plate part 2 by attaching the second frame body 20 to the bottom plate part 2, it is easy to assemble the cell screening device 1. After use, it is also possible to remove the second frame body 20 from the bottom plate part 2, which facilitates maintenance.

Further, in this embodiment, the cell placement membrane 6, the lid part 14, and the peripheral wall portion 22 can be accurately positioned simply by forming the bottom plate part 2, the second frame body 20, and the first frame body 36 as separate ones and attaching the first frame body 36 and the second frame body 20 to the bottom plate part 2, and thus the ease of assembly can be improved. After use, it is also possible to remove the frame body 36 and the second frame body 20 from the bottom plate part 2, which facilitates maintenance.

Further, in this embodiment, the cell placement part 6, the lid part 14, the peripheral wall portion 22, and two fluid injection ports 16 can be accurately positioned simply by forming the bottom plate part 2 and the second frame body 20 as separate ones, and attaching the second frame body 20 to the bottom plate part 2, and thus assembly is easy.

Further, in this embodiment, since the fluid injection port 16 has a cylindrical shape, it is easy to inject in and take out the fluid by almost airtightly applying a conical pointed tip of a pipette to the opening portion 16A, a dispenser, or the like.

According to the cell screening kit of this embodiment, in a state where the cells C are incorporated into the individual wells 50, detection particles B and secretion product of cells are reacted in the wells 50, and screening can be carried out by luminescence from the detection particles B. Moreover, even in a case where the cell screening device 1 is carried or inclined with a fluid such as a dispersion liquid being put into the flow channel 10, it becomes difficult for the fluid to move along the flow channel 10, and it is possible to suppress a problem in which some of the dispersion liquid flows into the wells 50 through the through-hole 52 and the cells C or the detection particles B caught in the wells 50 are released from the wells 50.

Figure 9:
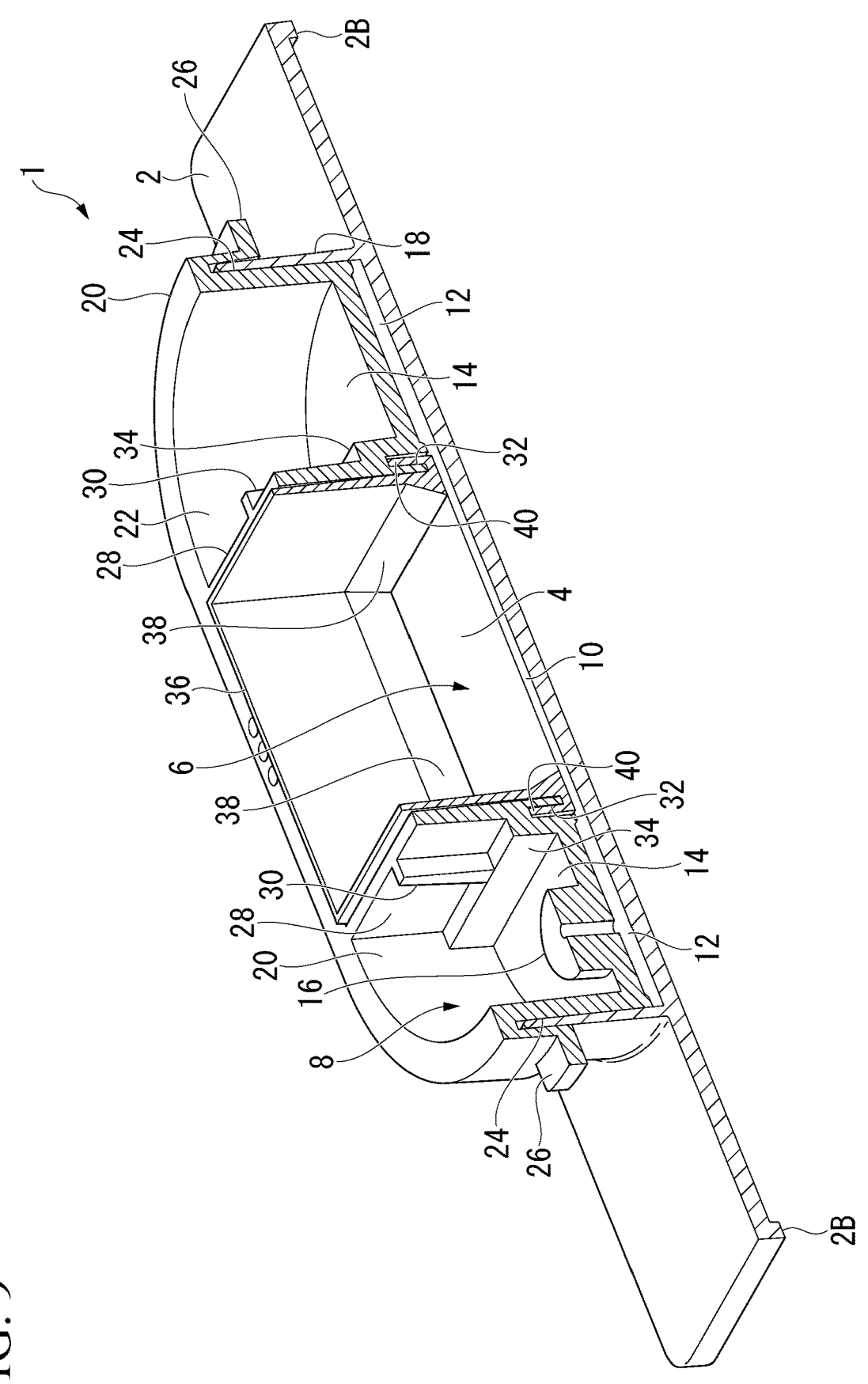
FIG. 9 is a perspective view showing a real cross section of a cell screening device according to another embodiment of the present invention.

The above embodiment has the constitution in which the fluid injection port 16 is provided at both ends of the cell screening device 1; however, as shown in FIG. 9, a constitution in which the fluid injection port 16 is provided in the lid part 14 at one end of the cell screening device 1 is also possible. In this case, the fluid can be injected in and taken out through only one fluid injection port 16.

Figure 10:
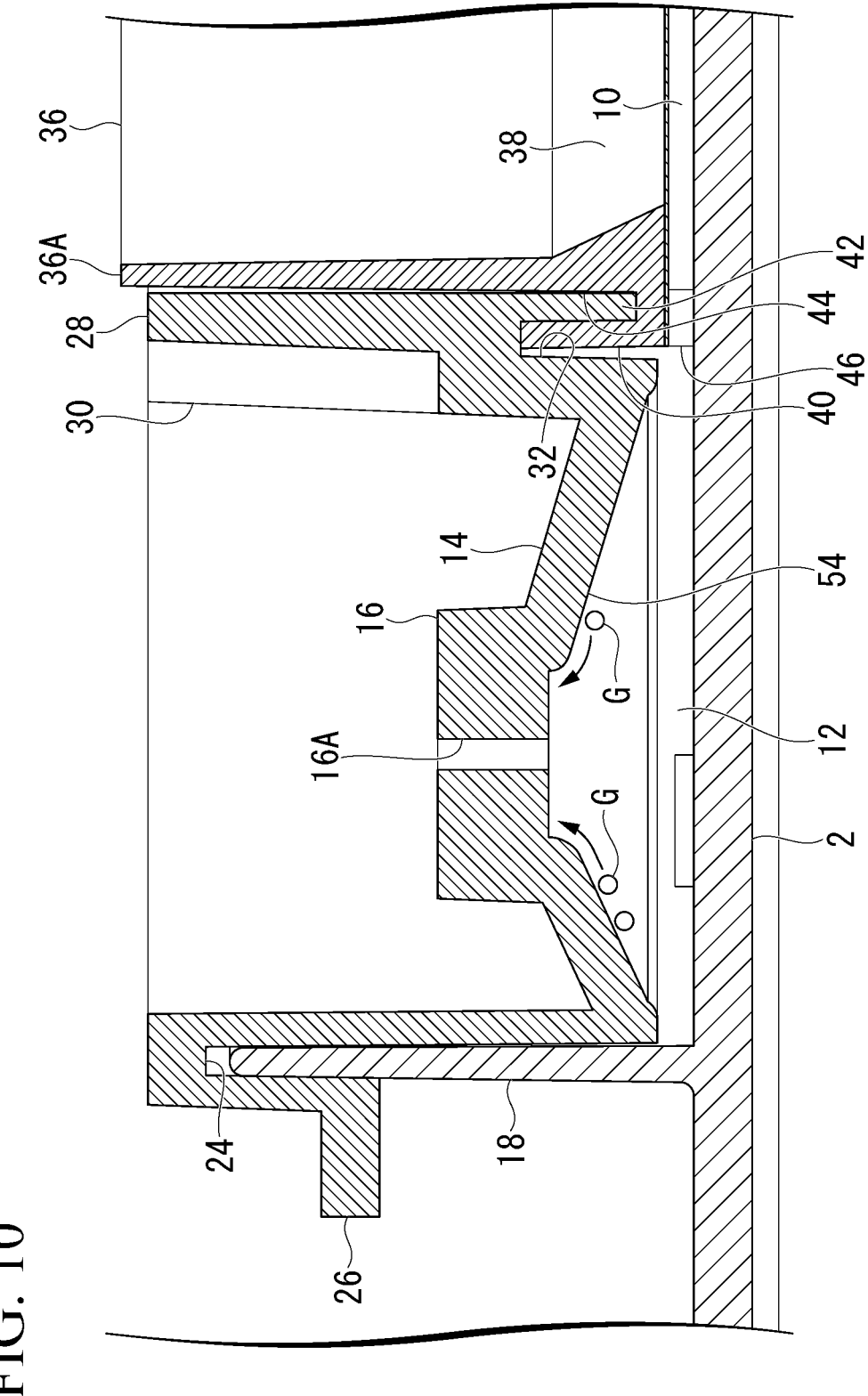
FIG. 10 is a real cross-sectional view showing an end part of the cell screening device according to the other embodiment of the present invention.

Further, in the above embodiment, the lid part 14 has a planar shape. However, as shown in FIG. 10, in the lid part 14, it is also possible to form a bubble discharge surface 54 that rises in an inclined surface shape or a stepped shape as the bubble discharge surface approaches the fluid injection port 16, on at least a part of a ceiling surface of the flow channel end part 12. In this case, since the ceiling surface on the back side of the lid part 14 rises toward the fluid injection port, the air bubbles G that have entered the flow channel end part 12 rise along the inclined surface 54 and become easily discharged from the fluid injection port 16, whereby it is possible to suppress problems such that, for example, the through-hole 52 is blocked by the air bubble G.

INDUSTRIAL APPLICABILITY

According to the cell screening device or the cell screening kit of the present invention, even in a case where the cell screening device is carried or inclined with the cells being caught in the well of the cell screening device and a fluid such as a dispersion liquid being put into the flow channel, it becomes difficult for the fluid to move along the flow channel, whereby the sloshing phenomenon is suppressed, and it is possible to suppress problems such that, for example, some of the dispersion liquid flows into the well through the through-hole and the cells or the detection particles caught in the well are released. As a result, the present invention can be industrially applicable.

REFERENCE SIGNS LIST

1: Cell screening device
2: Bottom plate part
4: Cell placement surface
6: Cell placement membrane (cell placement part)
8: Fluid injection part
10: Flow channel
12: Flow channel end part
14: Lid part (fluid storage part)
16: Fluid injection port
16A: Opening portion
18: Engagement wall
20: Second frame body
22: Peripheral wall portion
24: Engagement groove
26: Protrusion
28: Partitioned part
30: Rib
32: Engagement groove
34: Step portion
36: First frame body
36A: Wall
38: Inclined surface
40: Engagement ridge
42: Engagement ridge
44: Engagement groove
46: Spacer 47: Notch
50: Well
52: Through-hole
54: Inclined surface (bubble discharge surface)
C: Cell
B: Bead
L: Dispersion liquid
G: Air bubble

The invention claimed is:

1. A cell screening device, comprising:

a bottom plate having a rectangular shape and having a spacer formed in an upper part thereof;

an outer frame body that has a peripheral wall, the peripheral wall comprising a rectangular wall portion in plan view and a pair of end wall portions, the outer frame body being detachably attached to an upper surface of the bottom plate;

a tubular frame body having a rectangular shape in plan view that is detachably accommodated in the rectangular wall portion of the peripheral wall of the outer frame body;

a cell placement membrane that is supported by the outer frame body on the spacer of the bottom plate so as to form a flow channel between the cell placement membrane and the bottom plate and has a cell placement surface thereon;

a pair of lid portions, each lid portion being provided in the outer frame body apart from the tubular frame body and the cell placement membrane, each lid portion being formed on a side of the cell placement membrane on the bottom plate in a longitudinal direction of the bottom plate;

a pair of flow channel end parts formed between each of the lid portions and the bottom plate and communicating with the flow channel;

a pair of fluid injection ports, each fluid injection port being provided to stand on an upper surface of one of the lid portions and having an opening communicating with its respective flow channel end part through its respective lid portion; and a plurality of wells formed in the cell placement membrane to open on the cell placement surface and having a size in which cells to be screened are individually accommodatable;

a through-hole that is formed in an inner bottom surface of each of the wells to reach the flow channel and has an inner diameter through which the cells to be screened are not passable;

a fluid storage that is formed lower than the opening of the fluid injection port on the upper surface of the lid around the fluid injection port so as to store a fluid that overflows from the opening of the fluid injection port; and a partition that is formed in the outer frame body between the tubular frame body and the lid so as to prevent the fluid stored in the fluid storage from flowing to the cell placement membrane, wherein the tubular frame body has an engagement groove that is formed on an outer circumference lower end surface of the tubular frame body so as to open upward, the outer frame body has an engagement ridge that is formed on a lower end of the outer frame body so as to protrude downward, and the engagement ridge is inserted into the engagement groove so that the tubular frame body is detachable downward with respect to the outer frame body.

2. The cell screening device according to claim 1, wherein the plurality of the wells are formed in the cell placement membrane in a lattice form, the cell placement membrane is stretched over the lower end of the tubular frame body, and an engaging part is provided on the outer frame body for detachably fixing the first tubular frame body on the bottom plate.

3. The cell screening device according to claim 2, wherein the outer frame body has a space for accommodating the tubular frame body, and the tubular frame body that supports the membrane body is detachably fixed inside the space of the outer frame body.

4. The cell screening device according to claim 1, wherein the fluid injection port has a cylindrical shape.

5. The cell screening device according to claim 1, wherein each lid portion has a bubble discharge surface formed on at least a part of a lower surface of the lid that is a ceiling surface of the flow channel end, the bubble discharge surface rises in an inclined surface shape or a stepped shape approaching the fluid injection port.

* * * * *